United States Patent
Tevet et al.

(10) Patent No.: US 11,056,212 B1
(45) Date of Patent: Jul. 6, 2021

(54) METHODS AND SYSTEMS FOR AN INTEGRATED DISASSEMBLER WITH A FUNCTION-QUEUE MANAGER AND A DISASSEMBLY INTERRUPTER FOR RAPID, EFFICIENT, AND SCALABLE CODE GENE EXTRACTION AND ANALYSIS

(71) Applicant: Intezer Labs, Ltd., Tel Aviv-Jaffa (IL)

(72) Inventors: Itai Tevet, New York, NY (US); Roy Halevi, Tel Aviv-Jaffa (IL); Jonathan Abrahamy, Ramat Hasharon (IL); Ari Eitan, Tel Aviv-Jaffa (IL); David Tufik, Jerusalem (IL); Jay Rosenberg, Tel Aviv (IL)

(73) Assignee: Intezer Labs, Ltd., Tel Aviv-Jaffa (IL)

(*) Notice: Subject to any disclaimer, the term of this patent is extended or adjusted under 35 U.S.C. 154(b) by 0 days.

(21) Appl. No.: 16/731,195

(22) Filed: Dec. 31, 2019

(51) Int. Cl.
G06F 21/56 (2013.01)
G16B 20/00 (2019.01)
G06F 8/53 (2018.01)
G16B 50/00 (2019.01)

(52) U.S. Cl.
CPC .............. *G16B 20/00* (2019.02); *G06F 8/53* (2013.01); *G06F 21/564* (2013.01); *G16B 50/00* (2019.02); *G06F 21/56* (2013.01)

(58) Field of Classification Search
CPC ................................................ G06F 21/56–564
See application file for complete search history.

(56) References Cited

U.S. PATENT DOCUMENTS

| 2013/0185798 A1* | 7/2013 | Saunders | G06F 21/563 726/24 |
| 2014/0068768 A1* | 3/2014 | Lospinuso | G06F 21/561 726/23 |
| 2015/0186649 A1* | 7/2015 | Humble | G06F 21/564 726/23 |

OTHER PUBLICATIONS

Schwarz, et al., "Disassembly of Executable Code Revisited", 2002, IEEE, Proceedings of the Ninth Working Conference on Reverse Engineering (WCRE'02) (Year: 2002).*

* cited by examiner

*Primary Examiner* — Daniel B Potratz
(74) *Attorney, Agent, or Firm* — Reuven K. Mouallem; FlashPoint IP Ltd.

(57) ABSTRACT

The present invention discloses methods and systems for an integrated disassembler with a function-queue manager and a disassembly interrupter for rapid, efficient, and scalable code gene extraction and analysis. Methods include the steps of: upon receiving a target binary file, disassembling the target binary file into assembly code; extracting code fragments from the assembly code; as each code fragment is extracted, verifying each code fragment; upon availability, placing each verified code fragment in an extractor queue; and upon availability, submitting each code fragment in the extractor queue to a gene-analysis system having a code genome database. Alternatively, upon determining the extractor queue is empty or determining resources of the gene-analysis system are underutilized, transferring partially-verified code fragments to the extractor queue. Alternatively, upon receiving gene information regarding the target binary file from the gene-analysis system during disassembly, determining whether to terminate the step of disassembling based on the gene information.

12 Claims, 2 Drawing Sheets

Exemplary Embodiment

METHODS AND SYSTEMS FOR AN INTEGRATED DISASSEMBLER WITH A FUNCTION-QUEUE MANAGER AND A DISASSEMBLY INTERRUPTER FOR RAPID, EFFICIENT, AND SCALABLE CODE GENE EXTRACTION AND ANALYSIS

FIELD AND BACKGROUND OF THE INVENTION

The present invention relates to methods and systems for an integrated disassembler with a function-queue manager and a disassembly interrupter for rapid, efficient, and scalable code gene extraction and analysis.

Despite the rapid pace of technology in general, few industries today are as dynamic as that of cyber security. Attackers' techniques are constantly evolving, and along with them, the potential threat.

For security teams, the challenge remains not to keep up, but rather, to outpace them. It is a persistent struggle: a never-ending, record-setting marathon at a constant sprint. Even as security professionals rest, attackers are hard at work. The tools and approaches used must also adapt in order to stay a step ahead in defending their organizations. Malware classification, which encompasses both the identification and attribution of code, has the power to unlock many clues that aid security teams in achieving this.

Whether legitimate or malicious, nearly every software is composed of previously written code; the key to deeply understanding its nature and origins lies in discovering code that has appeared in previously known software. Reports on malware statistics indicate that there are around 350,000 new samples every day.

In order to determine if a file is benign/trusted or malicious, code fragments need to be identified in a source file before such fragments can be classified as code genes and analyzed. Typically, such files are binary files which need to be disassembled into assembly code containing instructions. This involves parsing the code into blocks from which code genes can be extracted representing at least one logic unit (i.e., from the start-block location/address to the stop-block location/address of a single block).

Software Reverse Engineering (SRE) relies on disassembling binary files using a disassembler (such as IDA Pro, RADARE, and GHIDRA). Such disassemblers identify the entry points of a binary file as the starting points for an assembly stream signature. The byte sequence of the code is disassembled into functions with their associated arguments. Disassembly is necessary if one wants to analyze a binary file in any meaningful way to determine its inherent functionality from a bitstream of indistinguishable zeroes and ones. By breaking the file into its component functions, each function can be analyzed and understood.

The goal of such disassembly can be multifold. Applications include ultimately searching for shared code genes by analyzing the genes with a database of known assembly-code fragments including both malicious and trusted code fragments. While disassemblers differ slightly, all disassemblers require a file to be fully disassembled before being able to further extract, normalize, and analyze such fragments for detection of code genes using a gene-analysis system, either trusted code or malware.

Using RADARE, one can analyze code of a function at a known address. However, one is limited to only the code fragments that are known in advance. A series of code fragments in an unknown file would require full disassembly before inspection of any one of the code fragments extracted, making such undertakings tediously manual and lacking scalability.

Given that there can be a very large number of such functions in a binary file, when code matching of genes is the goal, such disassemblers are slow, clumsy, and inefficient in processing a file, requiring manual entry and consuming valuable processing time. To appreciate the significance of efficiency and scalability, typically such code matching currently involves analyzing tens of billions of genes from tens of millions of files. Disassembling each binary file for extracting genes with current disassemblers would take around 16 years (calculated based on 10 seconds per file for 50M files).

It would be desirable to have methods and systems for an integrated disassembler with a function-queue manager and a disassembly interrupter for rapid, efficient, and scalable code gene extraction and analysis. Such methods and systems would, inter alia, overcome the various limitations mentioned above.

SUMMARY

It is the purpose of the present invention to provide methods and systems for an integrated disassembler with a function-queue manager and a disassembly interrupter for rapid, efficient, and scalable code gene extraction and analysis.

It is noted that the term "exemplary" is used herein to refer to examples of embodiments and/or implementations, and is not meant to necessarily convey a more-desirable use-case. Similarly, the terms "alternative" and "alternatively" are used herein to refer to an example out of an assortment of contemplated embodiments and/or implementations, and is not meant to necessarily convey a more-desirable use-case. Therefore, it is understood from the above that "exemplary" and "alternative" may be applied herein to multiple embodiments and/or implementations. Various combinations of such alternative and/or exemplary embodiments are also contemplated herein.

Embodiments of the present invention enable disassembly of binary code into assembly code by starting at one or more entry points, and continuing through other analysis points (such as blocks from jump commands and export calls). When a function is detected (i.e., when the end of the last block of a function, or the beginning of the first block of the next function, is found), the disassembled function can be accessed by a code-matching analysis program, without having to wait for all functions in the file to be fully disassembled. This saves substantial time in the overall detection and analysis of shared code genes. Moreover, once a code-matching analysis program has detected a requisite amount of gene information that the file contains, the disassembler can terminate the disassembly process during disassembly, saving valuable resources of the disassembler to process other files.

Such a disassembler makes the overall process of disassembly and gene analysis streamlined through automation of the extracted gene analysis as each function is separated from the binary file and becomes available. Each function can be addressed during the analysis stage, allowing for scalability to process bulk files. Both aspects provide significant enhancement in the ability to rapidly process binary files to analyze their code fragments for malicious and/or trusted genes in a shared code database.

Embodiments of the present invention provide a disassembler with an integrated Function-Queue Manager (FQM)

for submitting disassembled functions to be searched within a database of known shared genes, both trusted and malicious. Embodiments of the present invention further provide a disassembly interrupter for determining whether to terminate disassembling of a target binary file during disassembly based on the gene information.

The gene information regarding the target binary file is received from the gene-analysis system. Such gene information can include the total number of detected genes, the number of detected genes by category or type, the number of detected genes by gene criticality, severity, and/or importance, and/or the presence of detected genes by gene criticality, severity, and/or importance. Furthermore, the gene information can also include ancillary information about the file such as a current elapsed time for a given disassembly process.

Therefore, according to the present invention, there is provided for the first time a method for an integrated disassembler for code gene analysis, the method including the steps of: (a) upon receiving a target binary file, disassembling the target binary file into assembly code; (b) extracting individually-identifiable code fragments from the assembly code; (c) as each individually-identifiable code fragment is extracted, verifying each individually-identifiable code fragment; (d) upon availability, placing each verified individually-identifiable code fragment in an extractor queue; and (e) upon availability, submitting each individually-identifiable code fragment in the extractor queue to a gene-analysis system having a code genome database.

Alternatively, the step of placing includes placing only each individually-identifiable code fragment that has been completely verified to be a valid function.

More alternatively, the method further including the steps of: (0 upon determining each individually-identifiable code fragment has not been completely verified, placing each partially-verified individually-identifiable code fragment in a verification queue; (g) performing additional verification on each partially-verified individually-identifiable code fragment; and (h) upon successfully completing the additional verification on each partially-verified individually-identifiable code fragment, transferring each completely-verified individually-identifiable code fragment to the extractor queue.

Most alternatively, the method further including the step of: (i) upon determining the extractor queue is empty, transferring each partially-verified individually-identifiable code fragment to the extractor queue.

Most alternatively, the method further including the step of: (i) upon determining resources of the gene-analysis system are underutilized, transferring each partially-verified individually-identifiable code fragment to the extractor queue.

Alternatively, the method further including the step of: (f) upon receiving gene information regarding the target binary file from the gene-analysis system during disassembly, determining whether to terminate the step of disassembling based on the gene information.

According to the present invention, there is provided for the first time a system for an integrated disassembler for code gene analysis, the system including: (a) a CPU for performing computational operations; (b) a memory module for storing data; (c) a disassembly module configured for, upon receiving a target binary file, disassembling the target binary file into assembly code; (d) an extracting module configured for extracting individually-identifiable code fragments from the assembly code; (e) a verification module configured for, as each individually-identifiable code fragment is extracted, verifying each individually-identifiable code fragment; and (f) a function-queue manager configured for: (i) upon availability, placing each verified individually-identifiable code fragment in an extractor queue; and (ii) upon availability, submitting each individually-identifiable code fragment in the extractor queue to a gene-analysis system having a code genome database.

Alternatively, the function-queue manager is further configured for: (iii) placing only each individually-identifiable code fragment that has been completely verified to be a valid function.

More alternatively, the function-queue manager is further configured for: (iv) upon the verification module determining each individually-identifiable code fragment has not been completely verified, placing each partially-verified individually-identifiable code fragment in a verification queue; (v) performing additional verification on each partially-verified individually-identifiable code fragment by the verification module; and (vi) upon successfully completing the additional verification on each partially-verified individually-identifiable code fragment, transferring each completely-verified individually-identifiable code fragment to the extractor queue.

Most alternatively, the function-queue manager is further configured for: (vii) upon determining the extractor queue is empty, transferring each partially-verified individually-identifiable code fragment to the extractor queue.

Most alternatively, the function-queue manager is further configured for: (vii) upon determining resources of the gene-analysis system are underutilized, transferring each partially-verified individually-identifiable code fragment to the extractor queue.

Alternatively, the system further including: (g) a disassembly interrupter configured for, upon receiving gene information regarding the target binary file from the gene-analysis system during disassembly, determining whether to terminate the step of disassembling based on the gene information.

According to the present invention, there is provided for the first time a non-transitory computer-readable storage medium, having computer-readable code embodied on the non-transitory computer-readable storage medium, for an integrated disassembler for code gene analysis, the computer-readable code including: (a) program code for, upon receiving a target binary file, disassembling the target binary file into assembly code; (b) program code for extracting individually-identifiable code fragments from the assembly code; (c) program code for, as each individually-identifiable code fragment is extracted, verifying each individually-identifiable code fragment; (d) program code for, upon availability, placing each verified individually-identifiable code fragment in an extractor queue; and (e) program code for, upon availability, submitting each individually-identifiable code fragment in the extractor queue to a gene-analysis system having a code genome database.

Alternatively, the placing includes placing only each individually-identifiable code fragment that has been completely verified to be a valid function.

More alternatively, the computer-readable code further including: (f) program code for, upon determining each individually-identifiable code fragment has not been completely verified, placing each partially-verified individually-identifiable code fragment in a verification queue; (g) program code for performing additional verification on each partially-verified individually-identifiable code fragment; and (h) program code for, upon successfully completing the additional verification on each partially-verified individually-identifiable code fragment, transferring each completely-verified individually-identifiable code fragment to the extractor queue.

Most alternatively, the computer-readable code further including: (i) program code for, upon determining the extractor queue is empty, transferring each partially-verified individually-identifiable code fragment to the extractor queue.

Most alternatively, the computer-readable code further including: (i) program code for, upon determining resources of the gene-analysis system are underutilized, transferring each partially-verified individually-identifiable code fragment to the extractor queue.

Alternatively, the computer-readable code further including: (0 program code for, upon receiving gene information regarding the target binary file from the gene-analysis system during disassembly, determining whether to terminate the disassembling based on the gene information.

These and further embodiments will be apparent from the detailed description and examples that follow.

BRIEF DESCRIPTION OF THE DRAWINGS

The present invention is herein described, by way of example only, with reference to the accompanying drawings, wherein.

DESCRIPTION OF THE ILLUSTRATIVE EMBODIMENTS

The present invention relates to methods and systems for an integrated disassembler with a function-queue manager and a disassembly interrupter for rapid, efficient, and scalable code gene extraction and analysis. The principles and operation for providing such methods and systems, according to the present invention, may be better understood with reference to the accompanying description and the drawings.

Figure 1:
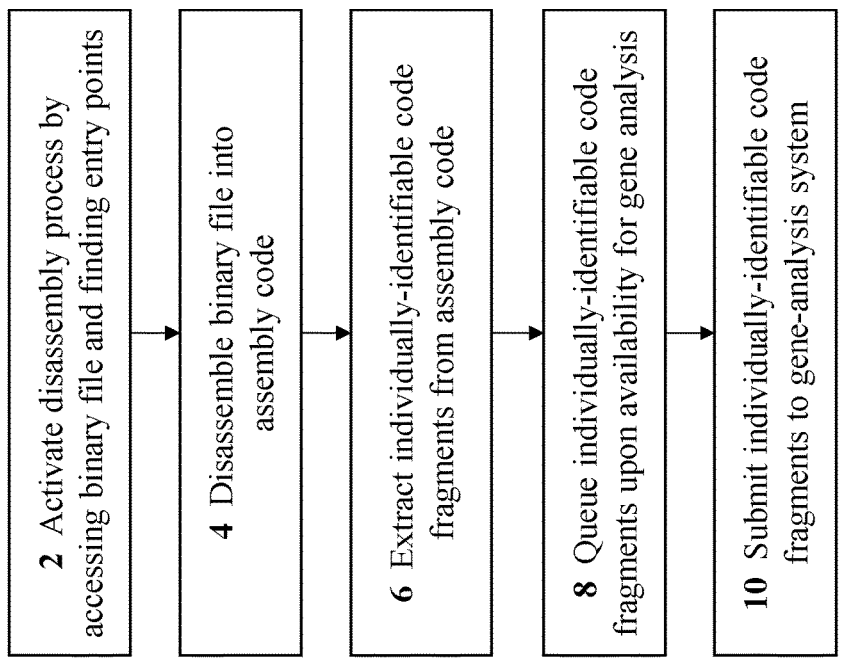
FIG. 1 is a simplified flowchart of the major process steps for an integrated disassembler for code gene extraction and analysis, according to embodiments of the present invention.

Referring to the drawings, FIG. 1 is a simplified flowchart of the major process steps for an integrated disassembler with a function-queue manager for code gene extraction and analysis, according to embodiments of the present invention. The process starts with activation of the disassembly process upon accessing a target binary file and finding the entry points (Step 2). The binary file is then disassembled into assembly code by finding instructions such as function calls or starts of loops (Step 4). Individually identified code fragments are extracted from the assembly code (Step 6). The individually-identifiable code fragments are then queued upon availability for gene analysis without requiring the entire binary file to be fully disassembled (Step 8). The individually-identifiable code fragments are then submitted to a gene-analysis system for determining whether the code fragments are trusted or malicious (Step 10).

Figure 2:
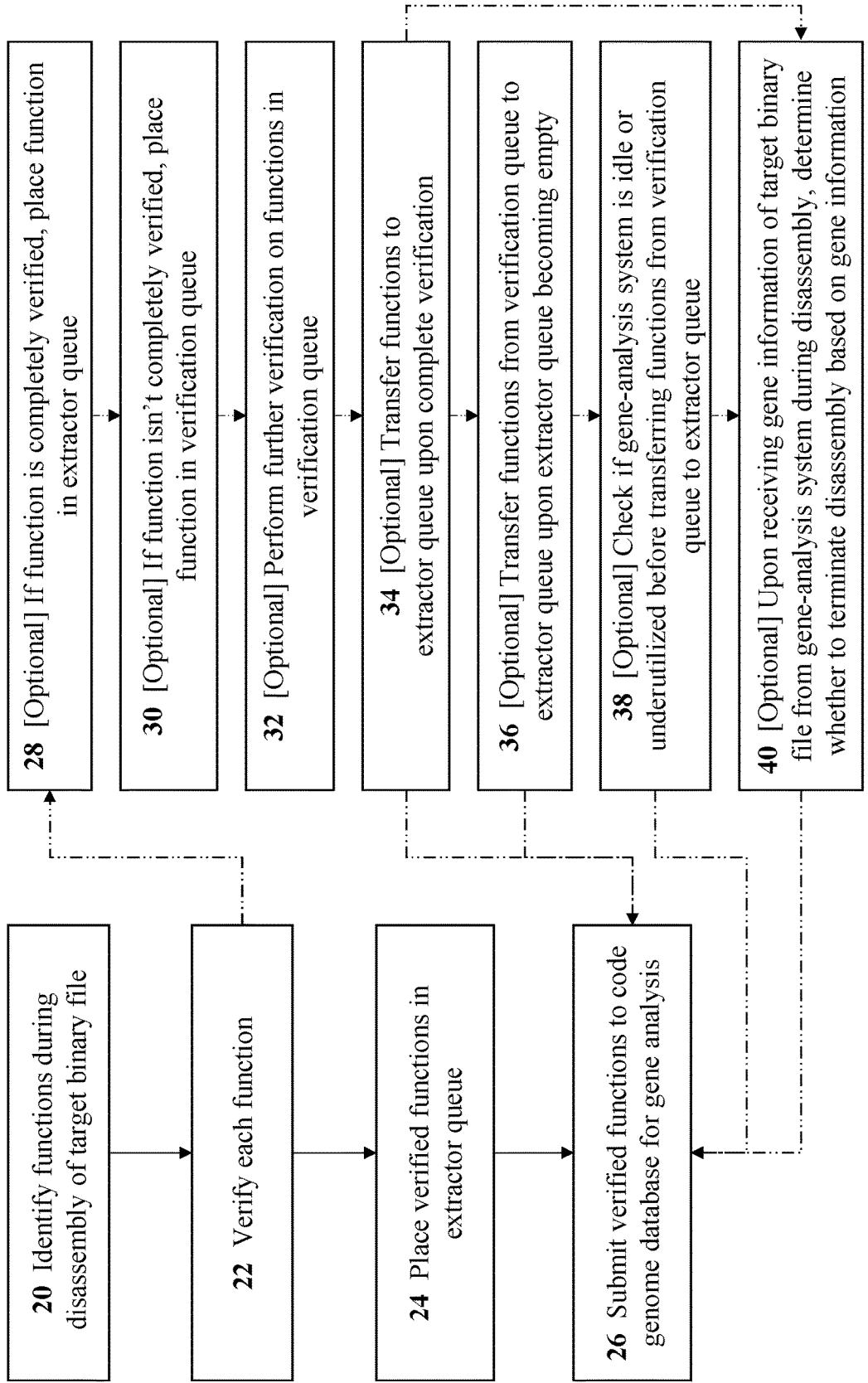
FIG. 2 is a simplified flowchart of the major process steps for the Function-Queue Manager (FQM) and disassembly interrupter, according to embodiments of the present invention.

The queuing of the code fragments for gene analysis upon availability in Step 8 is performed by an integrated function-queue manager of the disassembler. FIG. 2 is a simplified flowchart of the major process steps for the Function-Queue Manager (FQM) and scan interrupter, according to embodiments of the present invention. Once a function has been potentially identified during disassembly of target binary file (Step 20), each function is verified by the FQM (Step 22). Upon verification, the verified functions are placed in an extractor queue before transferring for gene analysis without waiting for the entire binary file to be disassembled (Step 24). Verified functions in the extractor queue are then submitted to the code gene database for code matching and gene analysis to identify trusted and malicious genes (Step 26).

In some embodiments, a function is only placed in the extractor queue if the function has been completely verified (Step 28). If a function hasn't been completely verified, the function is placed in a verification queue (Step 30). Functions in the verification queue undergo further verification to determine if they are truly valid, unique, and meaningful functions (Step 32). Functions in the verification queue are transferred to the extractor queue upon successfully completing verification (Step 34).

Alternatively, functions in the verification queue can also be transferred to the extractor queue upon the extractor queue becoming empty in order to prevent the gene-analysis system from becoming idle even without being completely verified (Step 36). Alternatively, the FQM can check if the gene-analysis system is idle or underutilized before transferring functions from verification queue to extractor queue (Step 38). Alternatively, upon receiving gene information of the target binary file from the gene-analysis system during disassembly, a disassembly interrupter can determine whether to terminate disassembly based on the gene information (Step 40). Finally, the process returns to Step 26 by submitting the verified functions to the gene-analysis system.

The disassembly interrupter prevents the disassembler from continuing to disassemble the target binary file unnecessarily once the gene-analysis system has obtained enough gene information regarding the file to categorize the nature of the file (e.g., known shared genes, trusted genes, and/or malicious genes), saving valuable resources of the disassembler to process other files. Examples of such gene information can include the total number of detected genes, the number of detected genes by category or type, the number of detected genes by gene criticality, severity, and/or importance, and/or the presence of detected genes by gene criticality, severity, and/or importance. Furthermore, the gene information can also include ancillary information about the file such as a current elapsed time for a given disassembly process.

While the present invention has been described with respect to a limited number of embodiments, it will be appreciated that many variations, modifications, and other applications of the present invention may be made.

What is claimed is:

1. A method for an integrated disassembler for code gene analysis, the method comprising the steps of:
   (a) upon receiving a target binary file, disassembling said target binary file into assembly code;
   (b) extracting individually-identifiable code fragments from said assembly code;
   (c) upon each said individually-identifiable code fragment being extracted, verifying said each individually-identifiable code fragment;
   (d) upon said each individually-identifiable code fragment being verified, placing each verified said individually-identifiable code fragment in an extractor queue, wherein said placing includes placing said each individually-identifiable code fragment that has been completely verified to be a valid function;

(e) upon said each verified individually-identifiable code fragment being placed in said extractor queue, submitting said each individually-identifiable code fragment in said extractor queue to a gene-analysis system having a code genome database;

(f) placing each partially-verified individually-identifiable code fragment in a verification queue, wherein said each partially-verified individually-identifiable code fragment has not been completely verified;

(g) performing additional verification on said each partially-verified individually-identifiable code fragment; and (h) transferring each completely-verified said individually-identifiable code fragment to said extractor queue.

2. The method of claim 1, the method further comprising the step of:

(i) transferring said each partially-verified individually-identifiable code fragment to said extractor queue when said extractor queue is empty.

3. The method of claim 1, the method further comprising the step of:

(i) transferring said each partially-verified individually-identifiable code fragment to said extractor queue when resources of said gene-analysis system are underutilized.

4. The method of claim 1, the method further comprising the step of:

(i) upon receiving gene information regarding said target binary file from said gene-analysis system during disassembly, determining whether to terminate said step of disassembling based on said gene information.

5. A system for an integrated disassembler for code gene analysis, the system comprising:

(a) a CPU for performing computational operations;

(b) a memory for storing data and having computer-readable code embodied therein, wherein said computer-readable code includes:

(i) program code for, upon receiving a target binary file, disassembling said target binary file into assembly code;

(ii) program code for extracting individually-identifiable code fragments from said assembly code;

(iii) program code for, upon each said individually-identifiable code fragment being extracted, verifying said each individually-identifiable code fragment;

(iv) program code for, upon said each individually-identifiable code fragment being verified, placing each verified said individually-identifiable code fragment in an extractor queue, wherein said placing includes placing said each individually-identifiable code fragment that has been completely verified to be a valid function;

(v) program code for, upon said each verified individually-identifiable code fragment being placed in said extractor queue, submitting said each individually-identifiable code fragment in said extractor queue to a gene-analysis system having a code genome database;

(vi) program code for placing each partially-verified said individually-identifiable code fragment in a verification queue, wherein said each partially-verified individually-identifiable code fragment has not been completely verified;

(vii) program code for performing additional verification on said each partially-verified individually-identifiable code fragment by said verification module; and (viii) program code for transferring each completely-verified said individually-identifiable code fragment to said extractor queue.

6. The system of claim 5, wherein said computer-readable code further includes:

(ix) program code for transferring said each partially-verified individually-identifiable code fragment to said extractor queue when said extractor queue is empty.

7. The system of claim 5, wherein said computer-readable code further includes:

(ix) program code for transferring said each partially-verified individually-identifiable code fragment to said extractor queue when resources of said gene-analysis system are underutilized.

8. The system of claim 5, said computer-readable code further includes:

(ix) program code for, upon receiving gene information regarding said target binary file from said gene-analysis system during disassembly, determining whether to terminate said step of disassembling based on said gene information.

9. A non-transitory computer-readable storage medium, having computer-readable code embodied on the non-transitory computer-readable storage medium, for an integrated disassembler for code gene analysis, the computer-readable code comprising:

(a) program code for, upon receiving a target binary file, disassembling said target binary file into assembly code;

(b) program code for extracting individually-identifiable code fragments from said assembly code;

(c) program code for, upon each said individually-identifiable code fragment is-being extracted, verifying said each individually-identifiable code fragment;

(d) program code for, upon said each individually-identifiable code fragment being verified, placing each verified said individually-identifiable code fragment in an extractor queue, wherein said placing includes placing said each individually-identifiable code fragment that has been completely verified to be a valid function;

(e) program code for, upon said each verified individually-identifiable code fragment being placed in said extractor queue, submitting said each individually-identifiable code fragment in said extractor queue to a gene-analysis system having a code genome database;

(f) program code for placing each partially-verified said individually-identifiable code fragment in a verification queue, wherein said each partially-verified individually-identifiable code fragment has not been completely verified;

(g) program code for performing additional verification on said each partially-verified individually-identifiable code fragment; and (h) program code for transferring each completely-verified said individually-identifiable code fragment to said extractor queue.

10. The non-transitory computer-readable storage medium of claim 9, the computer-readable code further comprising:

(i) program code for transferring said each partially-verified individually-identifiable code fragment to said extractor queue when said extractor queue is empty.

11. The non-transitory computer-readable storage medium of claim 9, the computer-readable code further comprising:

(i) program code for transferring said each partially-verified individually-identifiable code fragment to said extractor queue when resources of said gene-analysis system are underutilized.

12. The non-transitory computer-readable storage medium of claim 9, the computer-readable code further comprising:
(i) program code for, upon receiving gene information regarding said target binary file from said gene-analysis system during disassembly, determining whether to terminate said disassembling based on said gene information.

\* \* \* \* \*